United States Patent [19]

Schuldt et al.

[11] Patent Number: 4,725,270

[45] Date of Patent: Feb. 16, 1988

[54] FLUID CHANNELING PAD

[75] Inventors: Eric J. Schuldt; Mangalore R. Pai; Robert A. Wolff, all of Erie, Pa.

[73] Assignee: American Sterilizer Company, Erie, Pa.

[21] Appl. No.: 920,094

[22] Filed: Oct. 17, 1986

[51] Int. Cl.[4] .............................................. A61B 19/00

[52] U.S. Cl. .................................... 604/356; 269/322; 269/327; 128/132 D

[58] Field of Search ........................ 604/356, 357, 317; 128/132 D; 5/90, 484; 269/322, 327, 328

[56] References Cited

U.S. PATENT DOCUMENTS

| | | | |
|---|---|---|---|
| 590,188 | 9/1897 | Griffith et al. | 604/357 |
| 1,741,838 | 12/1929 | Gilbert | 604/357 |
| 1,900,255 | 3/1933 | Ormsbee | 269/327 |
| 1,930,398 | 10/1933 | Souchard | 604/356 |
| 1,970,754 | 8/1934 | Jonasen | 5/484 |
| 3,779,211 | 12/1973 | Etes | 269/327 |
| 4,216,774 | 8/1980 | Graber | 5/484 |

*Primary Examiner*—C. Fred Rosenbaum
*Assistant Examiner*—Denise Whelton
*Attorney, Agent, or Firm*—Kirkpatrick & Lockhart

[57] ABSTRACT

A fluid channelling pad is comprised of a padded portion for substantially covering a work surface. A member extends from the perimeter of the padded portion and has at least a portion thereof extending upwardly. The upwardly extending portion is displaced from the padded portion a predetermined distance to form a channel to control the flow of fluids.

20 Claims, 6 Drawing Figures

FLUID CHANNELING PAD

BACKGROUND OF THE INVENTION

Field of the Invention

The present invention is directed generally to pads for work surfaces and more specifically to pads used in conjunction with medical tables of the type used for surgery, delivering babies, examinations, etc.

Procedures performed on medical tables such as surgical procedures, the delivery of babies, patient examinations, etc. often involve the release of bodily fluids. Pads currently used on such medical tables have no ability to channel or in any way divert or control the flow of such fluids. These fluids often flow over the side and along the under surface of currently used pads The fluids then travel into the interior of the medical table.

Such seepage causes extreme cleaning and disinfecting problems. If the table and pad are not completely cleaned and disinfected, patients may develop infections. Additionally, seepage into the interior of the table may eventually effect the table mechanisms thereby degrading the performance of the table. Thus, a need exists for a pad which can control the flow of bodily fluids encountered during medical procedures to thereby eliminate cleaning and disinfecting problems, reduce the possibility of patient infection, and reduce the possibility of table malfunctions.

SUMMARY OF THE PRESENT INVENTION

The present invention is directed to a fluid channeling pad which is comprised of a padded portion for substantially covering a work surface. A member extends along the perimeter of the padded portion and has at least a portion thereof which extends upwardly. The upwardly extending portion is displaced from the padded portion a predetermined distance therefrom to form a channel. The channel controls the flow of fluids such that the fluids do not flow under the pad or into the table's mechanisms.

Various embodiments of the present invention are anticipated. In one embodiment, the member extending from the perimeter of the padded portion forms the channel with itself. According to such an embodiment, it is anticipated that the member may be V-shaped or U-shaped to form a channel along the perimeter of the table.

According to another embodiment of the present invention the member is shaped to form a channel with the padded portion. According to this embodiment, the member has a first portion extending substantially horizontally from the perimeter and a second portion extending substantially vertically upwardly from the first portion to form a substantially rectangular channel with the padded portion. According to another embodiment the member includes a member extending substantially diagonally upward from the perimeter to form a substantially V-shaped channel with the padded portion.

The shape of the member is maintained by using stiffeners which are continuous members. If the table with which the pad is being used is articulated, the stiffener may have a discontinuity at the point of articulation thereby enabling the pad to move with the table.

The channel formed by the pad of the present invention may end at the corners of the table so that the fluids flowing in the channel will have an outlet.

The present invention of a fluid channelling pad has a unique fluid-channeling feature for draining fluids away from the surgical or speciality medical table. The present invention prevents seepage of fluids encountered during surgical/examination procedures to the interior of the table thus alleviating cleaning/disinfecting problems, potential patient infection, and potential malfunctions of the medical table. These and other advantages and benefits of the present invention will become apparent from the Description of a Preferred Embodiment hereinbelow.

BRIEF DESCRIPTION OF THE DRAWINGS

In order that the present invention may be clearly understood and readily practiced, preferred embodiments will now be described, by way of example only, with reference to the accompanying figures wherein.

DESCRIPTION OF A PREFERRED EMBODIMENT

Figure 1:
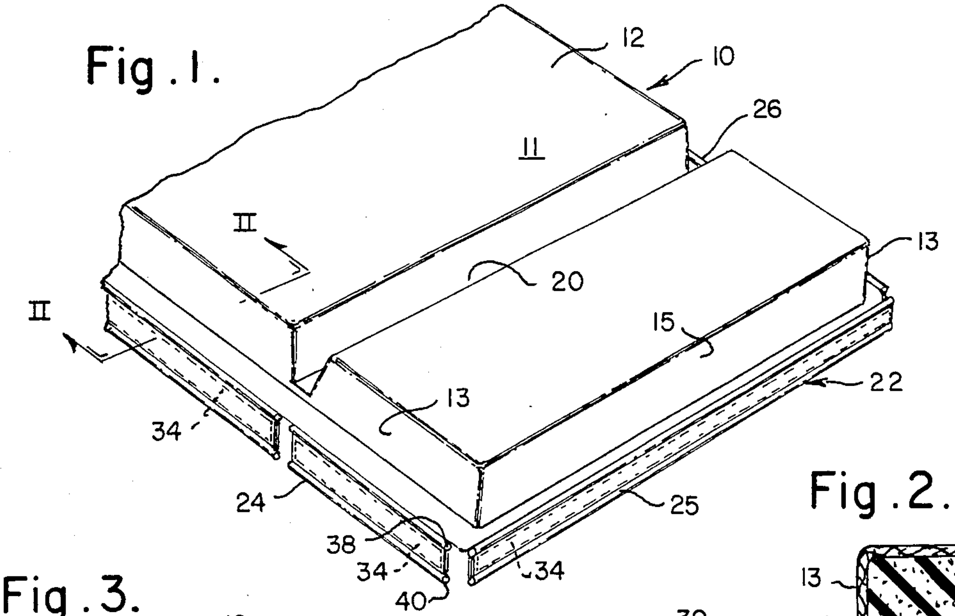
FIG. 1 is a perspective view of a portion of a pad constructing according to the teachings of the present invention.

Illustrated in FIG. 1 is a fluid channeling pad 10 constructed according to the teachings of the present invention. The pad 10 can be used to cover any work surface. As described more fully hereinbelow, the pad 10 may be used with a medical table such as a surgical table, delivery table, examination table, etc. wherein bodily fluids may contact the pad 10.

Figure 2:
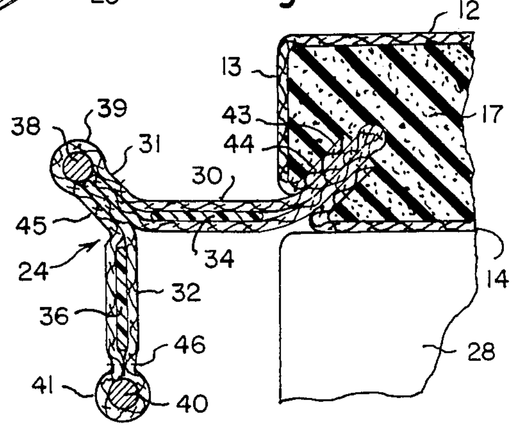
FIG. 2 is a cross-sectional view of the pad of FIG. 1 taken along the lines II—II.

The pad 10 has an upper surface 12, two side surfaces 13, one of which is seen in FIG. 1, a bottom surface 14 seen in FIG. 2, and two end surfaces 15, one of which is seen in FIG. 1. The surfaces 12–15 enclose a foam rubber material 17, seen in FIG. 2, or other cushion-like material in a known manner to form a padded portion generally designated by the reference number 11. The upper surface 12 has a trough-like portion 20. This trough-like portion 20 is located at a point on the medical table which is articulated. Because of the trough-like portion 20, the pad 10 is capable of articulating to conform to the surface of the table. The provision of a trough-like portion 20 for the pad 10 is known in the art and is not considered to be a feature of the present invention.

Extending substantially around the perimeter of the padded portion 11 is a fluid control channel 22. The fluid control channel 22 is comprised of four separate fluid control channels. As shown in FIG. 1 a first fluid control channel 24 extends along the left side 13 of the padded portion 11, second fluid control channel 25 extends along the end 15 of the padded portion 11, and a third fluid control channel 26 extends along the right side 13 of the padded portion 11. A fourth fluid control channel, not shown, extends along the end of the padded portion 11 which is not shown.

In FIG. 2, a cross-sectional view of the padded portion 11 positioned atop a medical table 28 is illustrated. The channel 24 illustrated in FIG. 2 is representative of the other channels 25 and 26 and is constructed of a single strip of material, typically the same type of material with which the padded portion 11 is constructed, that is folded as shown in FIG. 2. The material is folded to create a first member 30 which extends substantially horizontally from the perimeter of the padded portion 11. The first member 30 has an upturned portion 31. This upturned portion 31 cooperates with the left side 13 of the padded portion 11 to form a substantially rectangularly-shaped fluid control channel. A second member 32 extends substantially vertically downward from the distal end of the first member 30.

To keep the fabric forming the first member 30 and second member 32 in the desired configuration, a first stiffener 34 is positioned between the two layers of fabric forming the first member 30 and a second stiffener 36 is positioned between the two layers of fabric forming the second member 32. The stiffeners 34 and 36 may be continuous strips of plastic or the like. Stiffeners 34 and 36 may have a discontinuity, as shown in FIG. 1, at the point of articulation of the medical table to provide the channel 24 with the same degree of movement as that of the padded portion 11.

In addition to the stiffeners 34 and 36, a first cord 38, or the like, is provided at the junction between the distal end of the first member 30 and the second member 32. The fabric forming the members 30 and 32 is wrapped around the cord 38 to form a first welt 39. The welt 39 serves as a drip edge for fluids which may buildup within the channel. A second cord 40, or the like, is provided at the distal end of the second member 32. The fabric, when wrapped around the second cord 40, forms a second welt 41 which acts as an additional drip edge.

The material which forms the first member 30, first welt 39, second member 32, and second welt 41 may be stitched at points 43, 44, 45, and 46 so that the first stiffener 34, second stiffener 36, first cord 38, and second cord 40 are held in the proper positions. It is anticipated that reinforced rubber, fluid proof fabric, or other material used to construct the surfaces 12–15 of the padded portion 11 and the fluid control channels 24–26 will be sufficiently rigid such that the stitch points 43 and 44 will be formed in such a manner that the position of the fluid control channels is maintained. The stitching used at points 43, 44, 45, and 46 should be fluid-proof stitching which is sealed to prevent entry of fluids.

Depending upon the stiffness of the cords 38 and 41, it may be necessary to provide a discontinuity at the articulation points as illustrated in FIG. 1.

As seen in FIG. 1, the ends of the fluid control channels provide an exit for fluid traveling through the channels. Fluid exiting from the corners where the first fluid control channel 24 meets the second fluid control channel 25 will not be provided with the opportunity to seep under the pad 10 or into the mechanism of the table 28.

The fluid-channeling characteristic of the present invention can be incorporated into any type of pad needed to fit the configuration of the table top. The design of the present invention allows for flexibility and articulation of the entire pad with the table top. The fluid control channels may be positioned along the perimeter of any type of pad utilizing fluid-proof material. The channels are constructed using sealed, fluid-proof stitching. Channel configuration is maintained through the use of stiffeners and cords which form welts. The stiffeners and welting may be constructed with a discontinuity at the points of articulation of the pad, as required. The embodiment shown in FIGS. 1 and 2 allows the present invention to cover and protect any protruding parts of the table.

The fluid control channels of the present invention collect and divert fluids away from the table. The welts 39 and 41 together with the second member 32 act as drip edges to prevent fluids from flowing underneath the pad 10. The present invention therefore facilitates easy cleaning and disinfecting of the pad and reduces the time required for those operations. The present invention reduces the possibility of patient infection as well as the possibility of damage to the mechanisms of the table. Such a device represents a substantial advance over the prior art.

Illustrated in FIGS. 3–6 are alternative embodiments of the present invention. Where applicable, similar parts providing similar functions have been given the same reference numeral which was used in FIGS. 1 and 2.

Figure 3:
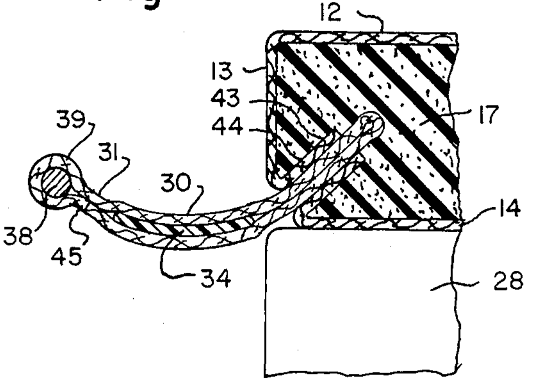
FIGS. 3–6 illustrate cross-sectional views of alternative embodiments of the present invention.

In FIG. 3, the embodiment illustrated is substantially the same as the embodiment illustrated in FIG. 2 with the exception that the second member 32 and second welt 41 have been eliminated.

Figure 4:
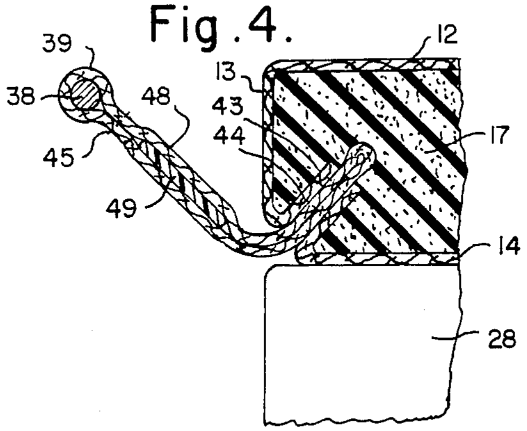

In FIG. 4, a first member 48 extends substantially diagonally from the perimeter of the padded portion 11. The member 48 has a stiffener 49 which provides the same function as the stiffeners 34 and 36 of FIG. 2. The member 48 ends in a welt 39 formed around the cord 38.

The embodiments shown in FIGS. 3 and 4 are embodiments wherein the members 30 and 48 extending from the perimeter of the padded portion 11 cooperate with the padded portion 11 to form the fluid control channel. Illustrated in FIGS. 5 and 6 are two embodiments wherein the fluid control channel is formed entirely by the protruding member such that the padded portion 11 is not relied upon to help form the fluid control channel.

Figure 5:
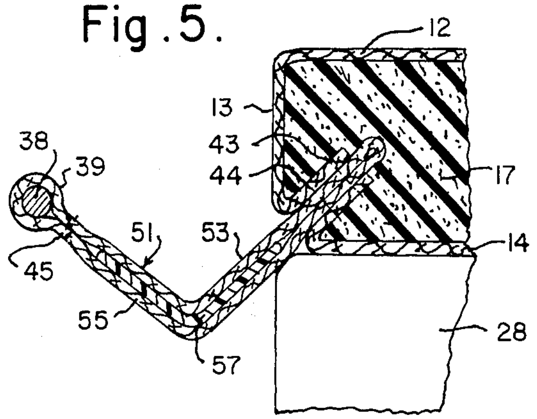

Turning to FIG. 5, a member 51 has a first portion 53 extending substantially diagonally downward from the perimeter of the padded portion 11 and a second portion 55 extending substantially diagonally upward from the end of the first portion to form a substantially V-shaped channel. A substantially V-shaped stiffener 57 is used to maintain the shape of the channel. The cord 38 is provided to form the welt 39 at the distal end of the member 51 which acts as a drip edge.

Figure 6:
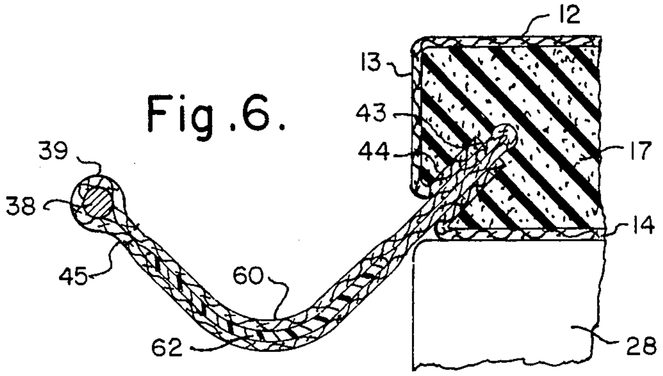

In FIG. 6 a substantially U-shaped member 60 forms a substantially U-shaped channel. A substantially U-shaped stiffener 62 is provided to maintain the shape of the channel. The cord 38 forms the welt 39 at the distal end of the member 60 which acts as a drip edge. The embodiments shown in FIGS. 5 and 6 are shaped such that it is impossible for fluids to flow along the underside of members 51 and 60 so as to contaminate the underside of the pad 14.

While the present invention has been described in connection with exemplary embodiments therof and in a medical environment, it will be understood that many modifications and variations will be readily apparent to those of ordinary skill in the art. This disclosure and the following claims are intended to cover all such modifications and variations.

What is claimed is:

1. A fluid channeling pad for use with an articulated medical table, comprising:

an articulate padded portion for substantially covering an articulated medical table, said padded portion being capable of moving with the medical table; and a member extending substantially along the perimeter of said padded portion, said member having at least a portion thereof extending upwardly, said portion being displaced from said padded portion a predetermined distance to form a collapsible channel for the flow of fluids.

2. The pad of claim 1 additionally comprising means for maintaining the shape of said member.

3. The pad of claim 2 wherein said means for maintaining includes a plastic stiffener.

4. The pad of claim 3 wherein said member is comprised of two layers of material connected together, and wherein said stiffener is positioned between said two layers.

5. The pad of claim 4 wherein said padded portion and said two layers of material include a padded portion and two layers of material constructed of a fluid resistant fabric.

6. The pad of claim 4 wherein said padded portion and said two layers of material include a padded portion and two layers of material constructed of reinforced rubber.

7. The pad of claim 4 wherein said connection of said two layers of material includes fluid proof stitching.

8. The pad of claim 7 additionally comprising means for sealing said stitching.

9. The pad of claim 1 additionally comprising a welt positioned at the end of said upwardly extending portion to form a drip edge.

10. The pad of claim 9 additionally comprising a cord, and wherein said welt is formed around said cord.

11. The pad of claim 1 additionally comprising a second member extending substantially downwardly from the end of said upwardly extending portion to form a drip edge.

12. The pad of claim 11 additionally comprising a stiffener for maintaining the shape of said second member

13. The pad of claim 11 additionally comprising a welt positioned at the end of said second member to form said drip edge.

14. The pad of claim 2 wherein said means for maintaining the shape of said member includes a continuous stiffener interrupted at the points of articulation.

15. The pad of claim 1 wherein said upwardly extending portion cooperates with said padded portion to form said channel.

16. The pad of claim 15 wherein said member includes a first portion extending substantially horizontally from said perimeter and a second portion extending substantially vertically upward from said first portion to form a substantially rectangular channel with said padded portion.

17. The pad of claim 15 wherein said member includes a member extending substantially diagonally upward from said perimeter to form a substantially V-shaped channel with said padded portion.

18. The pad of claim 1 wherein said upwardly extending portion cooperates with said member to form said channel.

19. The pad of claim 18 wherein said member includes a member having a first portion extending substantially diagonally downward from said perimeter and a second portion extending substantially diagonally upward from said first portion to form a substantially V-shaped channel.

20. The pad of claim 18 wherein said member includes a substantially U-shaped member extending from said perimeter to form a substantially U-shaped channel.

* * * * *

UNITED STATES PATENT AND TRADEMARK OFFICE
CERTIFICATE OF CORRECTION

PATENT NO. : 4,725,270

DATED : February 16, 1988

INVENTOR(S) : Eric J. Schuldt, Robert A. Wolff and Mangalore R. Pai

It is certified that error appears in the above-identified patent and that said Letters Patent is hereby corrected as shown below:

Col. 1, line 17, following "pads" insert --.--.

Col. 4, line 61, delete "articulate" and substitute therefor --articulated--.

Col. 5, line 2, following "for" insert --directing--.

Signed and Sealed this

Thirteenth Day of September, 1988

*Attest:*

DONALD J. QUIGG

*Attesting Officer*

*Commissioner of Patents and Trademarks*